US010071125B2

(12) United States Patent
Knol et al.

(10) Patent No.: US 10,071,125 B2
(45) Date of Patent: *Sep. 11, 2018

(54) NUTRITIONAL COMPOSITION WITH PROBIOTICS

(71) Applicant: N.V. Nutricia, Zoetermeer (NL)

(72) Inventors: Jan Knol, Utrecht (NL); Monique Haarman, Vriezenveen (NL); Johan Garssen, Utrecht (NL); Adrianus Johannes Maria Vriesema, Utrecht (NL); Martine Sandra Alles, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 7 days.

This patent is subject to a terminal disclaimer.

(21) Appl. No.: 15/088,639

(22) Filed: Apr. 1, 2016

(65) Prior Publication Data

US 2016/0206667 A1 Jul. 21, 2016

Related U.S. Application Data

(62) Division of application No. 11/817,102, filed as application No. PCT/NL2006/050040 on Feb. 28, 2006, now Pat. No. 9,314,047.

(30) Foreign Application Priority Data

Feb. 28, 2005 (EP) .................................. 05075486

(51) Int. Cl.
| | | |
|---|---|---|
| *A61K 35/74* | (2015.01) | |
| *A61K 35/745* | (2015.01) | |
| *A61K 35/747* | (2015.01) | |
| *A61K 9/00* | (2006.01) | |
| *A61K 31/715* | (2006.01) | |
| *A61K 35/742* | (2015.01) | |
| *A23L 33/00* | (2016.01) | |
| *A23L 33/135* | (2016.01) | |
| *A23L 33/21* | (2016.01) | |

(52) U.S. Cl.
CPC .......... *A61K 35/745* (2013.01); *A23L 33/135* (2016.08); *A23L 33/21* (2016.08); *A23L 33/40* (2016.08); *A61K 9/0095* (2013.01); *A61K 31/715* (2013.01); *A61K 35/742* (2013.01); *A61K 35/747* (2013.01); *A23V 2002/00* (2013.01); *A23Y 2220/63* (2013.01); *A23Y 2300/29* (2013.01)

(58) Field of Classification Search
None
See application file for complete search history.

(56) References Cited

U.S. PATENT DOCUMENTS

| 6,451,584 | B2 | 9/2002 | Tomita et al. |
| 7,601,364 | B2 | 10/2009 | Sawatzki et al. |
| 2002/0015990 | A1 | 2/2002 | Tomita et al. |
| 2004/0062758 | A1 | 4/2004 | Mayra-Makinen et al. |

FOREIGN PATENT DOCUMENTS

| DE | 10206995 A1 | 9/2003 |
| EP | 1 105 002 B1 | 6/2001 |
| EP | 1 175 905 A1 | 1/2002 |
| EP | 1 374 878 A1 | 1/2004 |
| EP | 1 481 682 A1 | 12/2004 |
| WO | WO-03/071883 A1 | 9/2003 |
| WO | WO-2005/039319 A2 | 5/2005 |

OTHER PUBLICATIONS

Bouhnik, et al. "Short-Chain Fructo-Oligosaccharide Administration Dose-Dependently Increases Frecal Bifidobacteria in Healthy Humans", The Journal of Nutrition, Jan. 1999, vol. 129, No. 1, pp. 113-116.
Dubey, et al. "Effect of Bifidogenic Factors on Growth Characteristics of Bifidobaceria in Infant Formulas", J. Dairy Sci, 1996, vol. 79, pp. 1156-1163.
Dubey, et al. "Growth Characteristics of Bifidobacteria in Infant Formulas", J. Dairy Sci., 1996, vol. 79, pp. 1145-1155.
International Search Report for PCT/NL2006/050040 dated Sep. 9, 2006, 4 pages.
Kitajima et al., Archives of Disease in Childhood 1997; 76: pp. F101-F107.
Moro et al., "Dosage-Related Bifidogenic Effects of Galacto- and Fructooligosaccharides in Formula-Fed Term Infants," Journal of Pediatric Gastroenterology and Nutrition, vol. 34, No. 3, pp. 291-295. (2002).
Savino et al., "Minor feeding problems during the first month of life: effect of a partially hydrolysed milk formula containing fructo- and galacto-oligosaccharides," Acta Paediatrica, Sep. 2003, pp. 86-90, Universitetsforlaget, Oslo, Norway.
Tanaka et al., Bifidobacteria Microflora 1983;2:17-24)0.
Thibault et al., Journal of Pediatric Gastroenterology and Nutrition, vol. 39, 2004, pp. 147-152.

*Primary Examiner* — Irene Marx
(74) *Attorney, Agent, or Firm* — Gilberto M. Villacorta; Sunit Talapatra; Foley & Lardner LLP

(57) ABSTRACT

A composition comprising *Bifidobacterium breve*, a non-digestible saccharide A and a non-digestible saccharide B, optionally combined with *Lactobacillus paracasei* and the use of said composition for the treatment and/or prevention of gastro-intestinal disorder, immune disorder and/or endocrine disorder.

17 Claims, 1 Drawing Sheet
Specification includes a Sequence Listing.

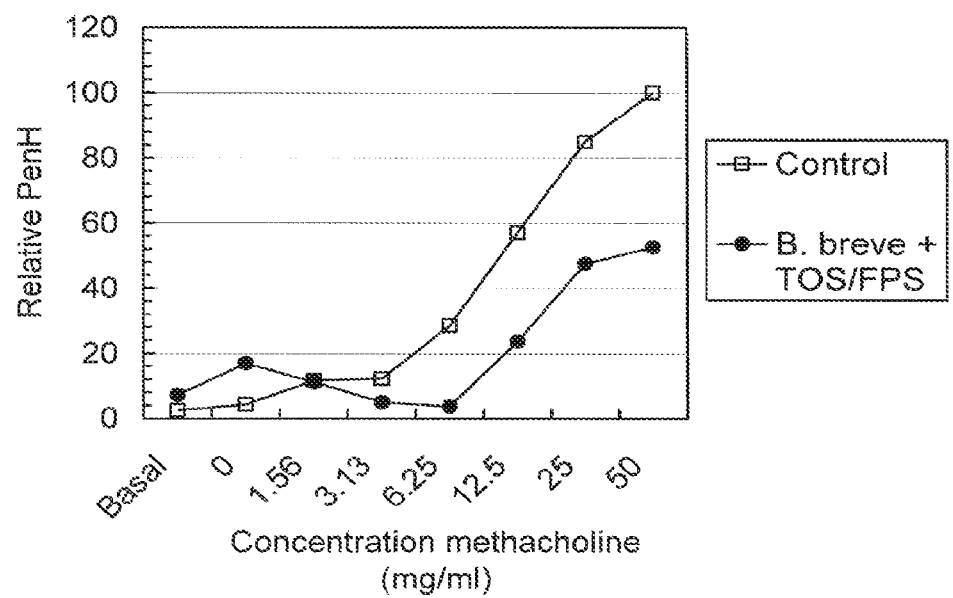

SEQUENCE LISTING

```
<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaagagccc aaaccaagtg att                                            23

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttcccagat aattcaacta tcgctta                                        27

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
taccactttg cagtcctaca                                                20
```

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctataagtaa gctttgatcc ggagattt                                      28

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttcctgcgg gtactgagat gt                                            22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
acaagctatg aattcacttg c                                             21

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cacttgtacg ttgaaaactg aatatcttaa                                    30

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgaactctct cggtcgcttt                                               20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ccgagaatca ttgagatc                                                 18

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaccgagaac accgcgttat                                               20

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acttaacctt actgatcgta gatcagtca                                     29

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
taatcgcata ctcaactaa                                                19

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acatcagtgt attgcttgtc agtgaatac                                     29

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctgcgggta ctgagatgtt tc                                            22

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tgccgccggc cag                                                      13

<210> SEQ ID NO 16
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggatcacct cctttctaag gaat                                            24

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgttctcggt ttcattatga aaaaata                                         27

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
acattcttcg aaactttgt                                                  19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
accgagaaca ccgcgttatt t                                               21

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cataacttaa cctaaacaat caaagattgt ct                                   32

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
atcgctaact caattaat                                                   18

<210> SEQ ID NO 22
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggctggatc acctcctttt                                                     19

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcttgagggt aatcccctca a                                                   21

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
cctgcacaca cgaaa                                                          15

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tggatgcctt ggcactagga                                                     20

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaatctccgg atcaaagctt acttat                                              26

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
tattagttcc gtccttcatc                                                     20

<210> SEQ ID NO 28
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 28
tcctacggga ggcagcagt                                                       19

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggactaccag ggtatctaat cctgtt                                               26

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cgtattaccg cggctgctgg cac                                                  23
```

NUTRITIONAL COMPOSITION WITH PROBIOTICS

CROSS-REFERENCE TO RELATED APPLICATIONS

This application is Divisional of U.S. patent application Ser. No. 11/817,102, filed Jan. 23, 2008, now U.S. Pat. No. 9,314,047, issued Apr. 19, 2016, which is the National Phase of International Patent Application No. PCT/NL2006/050040, filed Feb. 28, 2006, published on Aug. 31, 2006 as WO 2006/091103 A2, which claims priority to European Patent Application No. 05075486.0, filed 28, 2005. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Mar. 30, 2016, is named 069818-9001SequenceListing.txt and is 7 KB.

TECHNICAL FIELD OF THE INVENTION

The present invention relates to nutritional compositions comprising at least two different non-digestible prebiotic saccharides and at least one probiotic bacterium. The nutritional composition is particularly suitable for feeding infants.

BACKGROUND OF THE INVENTION

Infants are devoid of intestinal flora at birth. As a result of contact with the mother during birth and subsequent feeding with human milk or formula milk, the intestinal flora rapidly develops. During the development, the intestinal flora is still immature and its equilibrium is fragile. Human milk-fed infants are less afflicted by infections or diseases than formula-fed infants. Hence, human milk-fed babies have less gastro-intestinal infections in terms of both incidence and duration, less atopic diseases such as allergy, eczema, less colics and cramps, and less constipation than formula-fed infants. Also afflictions occurring later in life, such as childhood obesity, diabetes, and asthma are related to the type of feeding during the earliest stages of life, with the human milk-fed infants being in the advantage.

Generally, the intestinal flora of human milk-fed infants is primarily composed of Bifidobacteria and Lactobacilli. Human milk contains human milk oligosaccharides, which are a growth factor for Bifidobacteria in the intestine of infants. The flora of formula-fed infants is more diverse and contains in general more *Bacteroides, Clostridium* and Enterobacteriaceae species. Formula-fed infants have about one-tenth to roughly two-third the number of Bifidobacteria of human milk-fed infants. Bifidobacteria and Lactobacilli are considered to be important in maintaining a well-balanced intestinal microbiota and it has been postulated that Bifidobacteria and Lactobacilli have several health-promoting effects, including the prevention and/or treatment of diarrhoea and intestinal infections. Furthermore, Bifidobacteria and Lactobacilli have been shown to play a role in the immune system of the host.

The approach up to now was to promote Bifidobacteria in general, i.e. on the genus level. The genus *Bifidobacterium* consists of many different species, which differ in metabolism, enzyme activity, oligo- and polysaccharide utilisation, cell wall composition, and interaction with the host's immune system. Therefore, not every species of *Bifidobacterium* has the same functional effect on the infant. *B. adolescentis* is more prevalent in the flora of adults and allergic infants, and is less common in faeces of healthy infants. *B. animalis/B. lactis* is not naturally occurring in humans. In healthy infants the Bifidobacteria flora is mainly composed of *B. infantis, B. breve* and *B. longum*. It is the aim of the present invention to achieve a flora in formula-fed infants that is reminiscent to the flora of human milk-fed babies on a *Bifidobacterium* species level.

EP1105002 describes the use of two different non-digestible carbohydrates to improve the intestinal flora. The carboydrates may especially comprise galacto-oligosaccharides and fructo-poly saccharides.

SUMMARY OF THE INVENTION

The present inventors have found that feeding a human infant a combination of different non-digestible saccharides increases the level of Bifidobacteria in faeces and regulates the Bifidobacteria population in the intestinal tract on a species level to a level which is similar to the levels observed in human milk fed infants, i.e. low in *B. catenulatum, B. pseudocatenulatum*, and *B. adolescentis*. However, the concentration of *Bifidobacterium breve* (*B. breve*) was found to be low relative to the human milk fed infants.

Hence in one aspect, the present invention provides a composition comprising non-digestible saccharides A and non-digestible saccharide B and *B. breve*. This composition can be advantageously used to equalise the Bifidobacteria species distribution in the gastrointestinal tract of a formula-fed infant.

In a further aspect it was also found that feeding infant formula containing a combination of different non-digestible saccharides increases the level of Lactobacilli in faeces and regulates the Lactobacilli population in the intestinal tract on a species level to a level which is similar to the levels observed in human milk fed infants. However, the concentration of *Lactobacillus paracasei* (*L. paracasei*) was found to be low relative to the human milk fed infants. Hence in a further aspect the present invention provides a composition comprising *B. breve* and *L. paracasei*, preferably combined with non-digestible saccharide A and non-digestible saccharide B. It was found that the populations of these bacteria are underdeveloped in the gastrointestinal tract of infants receiving infant formula. Hence, this combination of probiotic bacteria can be advantageously used for feeding infants and simulate the intestinal flora of a human milk-fed infant.

FIGURE LEGEND

FIG. 1: Plot of airway hyperresponsiveness as relative PenH (enhanced pause) versus the methacholine concentration in mice receiving a combination of *B. breve*, transgalacto-oligosaccharides and fructopolysaccharides; and a control group of mice receiving saline.

DETAILED DESCRIPTION OF THE INVENTION

The present invention provides a composition having a viscosity between 1 and 60 mPa·s, a caloric density between 10 and 250 kcal per 100 ml, comprising *Bifidobacterium breve*, a non-digestible saccharide A and a non-digestible saccharide B, wherein:

a. non-digestible saccharide A has a degree of polymerisation between 2 and 200 and at least 60 mol % of the total monosaccharide units of saccharide A are monosaccharides selected from galactose, fructose and glucose monosaccharides; and
b. non-digestible saccharide B has a degree of polymerisation between 2 and 200 and at least 60 mol % of the total monosaccharide units of saccharide B are monosaccharides selected from galactose, fructose and glucose monosaccharides; and wherein
i) the percentage of at least one monosaccharide selected from the group consisting of glucose, fructose and galactose in saccharide A is at least 40 mol % higher than the percentage of the same monosaccharide in saccharide B; and/or
ii) the percentage of at least one glycosidic linkage of saccharide A based on total glycosidic linkages of saccharide A is at least 40% higher than the percentage of the same glycosidic linkage in saccharide B; and/or
iii) the degree of polymerisation of saccharide A is al least 5 monosaccharide units lower than the degree of polymerisation of saccharide B.

In a further aspect the present invention provides a composition comprising 5 to 16 en. % protein, 30 to 60 en. % fat, and 25 to 75 en. % carbohydrates comprising *Bifidobacterium breve* and *Lactobacillus paracasei*.

In still a further aspect the present invention provides the use of the present composition for the manufacture of a composition for normalisation of the *Bifidobacterium* and/or *Lactobacillus* species population in the gastro-intestinal tract of fed with non-human milk- or partially human milk to the *Bifidobacterium* and/or *Lactobacillus* species population of infants fed with human milk.

In a further aspect the present invention provides the use of the present composition for the manufacture of a composition for the prevention and/or treatment of a gastro-intestinal disorder, immune disorder and/or endocrine disorder, preferably cow's milk allergy and/or infection.

Viscosity

The present composition has a viscosity between 1 and 60 mPa·s, preferably between 1 and 20 mPa·s, more preferably between 1 and 10 mPa·s, most preferably between 1 and 6 mPa·s. The low viscosity ensures a proper administration of the liquid, e.g. a proper passage through the whole of a nipple. Also this viscosity closely resembles the viscosity of human milk. Furthermore, a low viscosity results in a normal gastric emptying and a better energy intake, which is essential for infants which need the energy for optimal growth and development. The present composition is preferably prepared by admixing a powdered composition comprising with water. Normally infant formula is prepared in such way. The present invention thus also relates to a packaged power composition wherein said package is provided with instruction to admix the powder with a suitable amount of liquid, thereby resulting in a liquid composition with a viscosity between 1 and 60 mPa·s.

The viscosity of the liquid is determined using a Physica Rheometer MCR 300 (Physica Messtechnik GmbH, Ostfilden, Germany) at shear rate of 95 $s^{-1}$ at 20° C.

*Bifidobacterium breve*

*Bifidobacterium breve* is a Gram-positive, anaerobic, branched rod-shaped bacterium. The present *B. breve* preferably has at least 95% identity of the 16 S rRNA sequence when compared to the type strain of *B. breve* ATCC 15700, more preferably at least 97% identity (Stackebrandt & Goebel, 1994, *Int. J. Syst. Bacteriol.* 44:846-849). The *Bifidobacterium* used in the present invention preferably hybridises with the *B. breve* probe and gives a signal with the 5' nuclease assay method as described further on in this document.

Preferred *B. breve* strains are those isolated from the faeces of healthy human milk-fed infants. Typically, these are commercially available from producers of lactic acid bacteria, but they can also be directly isolated from faeces, identified, characterised and produced. According to a preferred embodiment, the present composition contains at least one *B. breve* selected from the group consisting of *B. breve* Bb-03 (Rhodia), *B. breve* M-16V (Morinaga), *B. breve* R0070 (Institute Rosell, Lallemand), DSM 20091, and LMG 11613. Most preferably, the *B. breve* is *B. breve* M-16V (Morinaga).

The present composition preferably contains $10^2$ to $10^{13}$ colony forming units (cfu) *B. breve* per gram dry weight of the present composition, preferably $10^4$ to $10^{12}$, more preferably $10^5$ to $10^{10}$, most preferably from $10^5$ to $1\times10^9$ cfu *B. breve* per gram dry weight of the present composition.

Preferably, the present composition contains $10^4$ to $10^{12}$, more preferably from $10^5$ to $10^{11}$, most preferably from $10^7$ to $5\times10^{10}$ colony forming units (cfu) *B. breve* per g of the total of saccharide A and B.

The dose of *B. breve* according to the present invention is preferably administered at a daily dose of $10^2$ to $10^{13}$, more preferably from $10^5$ to $10^{11}$, most preferably from $10^8$ to $5\times10^{10}$ colony forming units (cfu).

Non-Digestible Saccharides

The present invention provides a composition which comprises non-digestible saccharide A and non-digestible saccharide B, hereinafter referred to as saccharide A and saccharide B respectively. Saccharide A and saccharide B are different saccharides and have different glycosidic linkages and/or degree of polymerisation and/or monosaccharide composition.

In addition to the monosaccharides galactose, fructose and glucose, the saccharides A and B may contain other monosaccharide units such as arabinose, xylose and mannose, up to a total of 40%. It is preferred, however, that at least 75%, more preferably at least 90%, or even at least 98 mol % of the total monosaccharide units of saccharide A and/or B are monosaccharides selected from galactose, fructose and glucose monosaccharides. It is preferred that the relative amount of α-linked glucose is below 30%, especially below 15%.

The term saccharide A as used in the present invention preferably refers to a mixture of non-digestible saccharides. The term saccharide B as used in the present invention preferably refers to a mixture of non-digestible saccharides. This is common practise, because the use of saccharides with e.g. one chain length is very expensive. Preferably and commonly, the members of such a mixture differ between one another in the number of the predominant monosaccharide only. When the saccharide A and/or B are saccharide mixtures, the averages of the respective parameters are used for defining the present invention. For example if saccharide A is a mixture of individual saccharides 25 wt. % Glu-Gal-Gal-Gal, 25 wt. % Glu-Gal-Gal and 50 wt. % Gal-Gal, the average monosaccharide composition is 85.4% Gal and 14.6% Glu. The average degree of polymerisation (DP) is 2.75.

The term non-digestible saccharide refers to saccharides that remain undigested in the gastrointestinal tract and reach the large intestine unabsorbed, i.e. saccharides that are not digested in the upper intestinal tract of a human, preferably a human infant e.g. not digested by the acids or enzymes present in the human intestinal tract. It is to be noted that digestible saccharides are not part of the saccharides A and B. Thus, for example glucose, fructose, galactose, sucrose, lactose, maltose and the maltodextrins are considered to be digestible.

Preferably saccharide A and B are water-soluble. Water-soluble saccharides are at least 50% water-soluble, according to a method described by L. Prosky et al, *J. Assoc. Anal. Chem* 71: 1017-1023, 1988.

In a preferred embodiment at least 80 wt. % of non-digestible saccharide A and B is fermentable. The term "fermentable" as used herein refers to the capability to undergo breakdown by micro-organisms in the lower part of the gastro-intestinal tract (e.g. colon) to smaller molecules, in particular short chain fatty acids and lactate. The fermentability of non-digestible saccharide A and B is preferably determined by the method described in *Am. J. Clin. Nutr.* 53, 1418-1424 (1991). In a more preferred embodiment at least 80 wt. % of non-digestible saccharide A and B are prebiotics. "Prebiotics" are defined as non-digestible food ingredients that selectively stimulate the growth and/or activity of one or more bacterial species in the colon and thereby beneficially affect the host (Gibson and Roberfroid, *J. Nutr.* 125:1401-1412(1995)).

Monosaccharide Composition

At least 60 mol %, preferably at least 75 mol %, more preferably at least 90 mol, most preferably at least 98 mol % of the total monosaccharide units of saccharide A and B are monosaccharides selected from galactose (gal), fructose (fru) and glucose (glu) monosaccharides. According to a preferred embodiment of the present invention, the percentage of at least one monosaccharide selected from the group consisting of glucose, fructose and galactose in saccharide A is at least 40 mol % higher than the percentage of the same monosaccharide in saccharide B, preferably at least 50 mol %, more preferably at least 75 mol %, even more preferably at least 90 mol %. An increased diversity of monosaccharides stimulates a wider population of beneficial intestinal bacteria.

Preferably at least 50 wt. %, preferably at least 75 wt. % of the cumulative weight of saccharide A and B are non-digestible saccharides with a DP of 2-8. By using a mixture with a high weight percentage of small saccharides the fermentability and stimulation effect on the growth of the lactic acid bacteria and Bifidobacteria will be increased.

The percentage of a monosaccharide in the saccharide can be simply calculated by dividing the amount of the respective monosaccharide unit (e.g. glucose) in the saccharide by the total amount of the monosaccharide units in that saccharide and multiply it by 100. When the saccharide is a saccharide mixture, the contribution of each individual saccharide in the saccharide mixture must be taken into account. The percentage of a saccharide mixture can be simply determined by completely hydrolysing the mixture and determining the molar percentage for each monosaccharide.

Preferably saccharide A contains at least 40 mol % galactose, more preferably at least 67 mol % galactose, more preferably at least 75 mol % galactose. Preferably saccharide B contains at least 30 mol % fructose, more preferably at least 67 mol % fructose, even more preferably at least 75 wt. % fructose.

For example, in the case where saccharide A is a mixture of glu-(gal)$_{n=2-7}$ with an average monosaccharide composition of 20 mol % glucose and 80 mol % galactose and saccharide B is a mixture of glu-(fru)$_{n=2-7}$ and (fru)$_{n2-7}$ with an average monosaccharide composition of 10 mol % glucose and 90 mol % fructose, the difference in a) glucose is 10 mol %; b) fructose is 90 mol %; and c) galactose 80 mol %. In this example galactose fulfils the criteria that the percentage of at least one monosaccharide selected from the group consisting of glucose, fructose and galactose in saccharide A is at least 40 mol % higher that the percentage of the same monosaccharide in saccharide B.

Degree of Polymerisation

Saccharide A and B have a degree of polymerisation (DP) between 2 and 200. Preferably at least 80 wt. %, more preferably at least 95 wt. %, most preferably at least 98 wt. % of the cumulative weight of saccharide A and B has a degree of polymerisation (DP) below 100, more preferably below 60, most preferably below 40. The lower DP advantageously reduces viscosity and increases fermentability of the non-digestible saccharides. Preferably at least 50 wt. %, preferably at least 75 wt. % of saccharide A are non-digestible saccharides with a DP of 2-8. By using a mixture with a high weight percentage of small saccharides, the fermentability and stimulation effect on the growth of the lactic acid bacteria and Bifidobacteria will be increased.

According to a preferred embodiment of the present invention, the DP of saccharide A is at least 5 monosaccharide units lower than the degree of polymerisation of saccharide B, preferably at least 10, even more preferably at least 15. Incorporation of a saccharide with an increased degree of polymerisation reduces the osmotic load, which is advantageous for an infant nutrition and improves prebiotic stimulation of the intestinal flora also at more distal parts of the colon.

Preferably, saccharide A has a DP of 2-15, more preferably 2-8. Preferably saccharide B has DP of 8-100. The saccharides A and B with a different DP may have the same or slightly different monosaccharide composition. When saccharides A and B have different DP and similar monosaccharide composition, then the difference in average DP between saccharide A and saccharide B is preferably at least 5, more preferably at least 10, even more preferably at least 15. Preferably, saccharide A and B have a different monosaccharide composition (see above) and a different DP.

For example, if saccharide A is a mixture of glu-fru$_{m=2-7}$ and fru$_{m=2-6}$ with an average DP of 4.5 monosaccharide units and saccharide B is glu-fru$_{n=12-100}$ with an average DP of 25 monosaccharide units; than the difference in the average DP (25−4.5=) 20.5.

Glycosidic Linkage

In a preferred embodiment of the present invention the percentage of at least one glycosidic linkage of saccharide A based on total glycosidic linkages of saccharide A is at least 40% higher the percentage of the same glycosidic linkage in saccharide B, preferably at least 50%, even more preferably at least 75%. The term "glycosidic linkage" as used in the present invention refers to a C—O—C linkage formed between the rings of two cyclic monosaccharides by the elimination of water. An increased diversity in glycosidic linkages stimulates a wider range of beneficial bacteria.

Glycosidic linkages differ in that they covalently bind carbon atoms in the monosaccharide units at differently numbered positions, and/or that they form α or β bonds. Examples of different glycosidic linkages occurring in non-digestible saccharides are β(1,3), α(1,4), β(2,1), α(1,2), and β(1,4) linkages.

Preferably the glycosidic linkages in saccharide A comprises at least 40% β(1,4) and/or β(1,6) glycosidic linkages, more preferably at least 75%. The glycosidic linkages in saccharide B preferably comprise at least 40% β(2,1) glycosidic linkages, more preferably at least 75%.

Combination

In a particularly preferred embodiment, the present saccharide A and B differ in at least two aspects selected from the group of glycosidic linkage, degree of polymerisation and monosaccharide composition. Preferably, the present saccharides A and B differ in degree of polymerisation and in at least one aspect selected from the group of glycosidic linkage and monosaccharide composition. More preferably, the present saccharide A and B differ in degree of polymerisation and monosaccharide composition. Most preferably all three aspects are different. The administration of mixtures of saccharides of different sizes, different "classes" and/or "structures" synergistically stimulate the intestinal flora, which advantageously influences health.

Concentration Saccharide A and B

The present composition preferably comprises at least 5 mg saccharide A per 100 ml, preferably at least 50 mg saccharide A per 100 ml, even more preferably at least 0.1 g saccharide A per 100 ml, most preferably at least 0.5 g saccharide A per 100 ml. Preferably the present composition does not contain more than 10 g saccharide A per 100 ml, preferably not more than 2.0 g per 100 ml. The present composition preferably comprises at least 5 mg saccharide B per 100 ml, preferably at least 10 mg saccharide B per 100 ml, even more preferably at least 25 mg saccharide B per 100 ml, most preferably at least 50 mg saccharide B per 100 ml. Preferably the present composition does not contain more than 10 g saccharide B per 100 ml, preferably not more than 1 g per 100 ml.

The weight ratio between saccharide A and saccharide B is preferably between 0.01 and 100, more preferably between 0.5 and 100, even more preferably between 4 and 100, most preferably between 24 and 99. A high weight ratio is particularly advantageous when saccharide A has a low DP and saccharide B has a relatively high DP. It ensures an optimal equilibrium between osmolality and fermentability.

Saccharide A and saccharide B preferably comprise between 5 and 100 wt. % based on the total weight of the non-digestible saccharides in the present composition, more preferably 50 to 100 wt. %.

Non-digestible saccharides A and B according to the present invention are preferably administered at a daily dose of 0.1 to 30 g (weight saccharide A+weight saccharide B), more preferably 0.5 to 15 g, more preferably 3 to 10 g.

Preferred Saccharides

Non-digestible saccharide A is preferably a saccharide selected from β-galactooligosaccharides, α-galactooligosaccharides, and (arabino-)galactans. According to a more preferred embodiment saccharide A is β-galactooligosaccharide, more preferably trans-galactooligosaccharide (TOS). Preferably saccharide A comprises β-galactooligosaccharides with β(1,4) and/or β(1,6) glycosidic bonds and a terminal glucose. TOS is for example commercially available under the tradename VIVINAL®GOS (Borculo Domo Ingredients, Zwolle, Netherlands).

Non-digestible saccharide B is preferably a saccharide selected from fructopolysaccharides and fructooligosaccharides. The terms fructopolysaccharides, polyfructose, polyfructan and fructan are interchangeably used herein and refer to polysaccharides comprising β-linked fructose units, which are preferably linked by β(2,1) and/or β(2,6) glycosidic linkages. Preferably, the fructopolysaccharide contains a terminal β(2,1) glycosidically linked glucose. Preferably, the fructopolysaccharide contains at least 7 β-linked fructose units. In a further preferred embodiment inulin is used as saccharide B. Inulin is a type of fructopolysaccharide wherein at least 75% of the glycosidic linkages are β(2,1) linkages. Typically, inulin has an average chain length between 8 and 60 monosaccharide units. Suitable fructopolysaccharide for use in the compositions is commercially available under the trade name, e.g. RAFTILINE®HP (Orafti).

In a further preferred embodiment, saccharide B is a fructooligosaccharide. A fructooligosaccharide is a saccharide comprising β-linked fructose units, which are preferably linked by β(2,1) and/or β(2,6) glycosidic linkages. The fructooligosaccharide preferably contains a β(2,1) glycosidic linked glucose at the reducing end. Preferably, the fructooligosaccharide contains 2 to 6 β-linked fructose units. A suitable source of fructooligosaccharide is RAFTILOSE® (Orafti), or Actilight (Beghin-Meiji).

Lactobacillus paracasei

In a preferred embodiment, the present composition comprises *Lactobacillus paracasei*. This bacterium has been found to be present in limited quantities in non-human milk-fed infants. Accordingly, the administration of a composition comprising non-digestible saccharide A, non-digestible saccharide B, *B. breve*, and *L. paracasei* enables the normalisation of Bifidobacteria on a species level, but also enables the normalisation of the *Lactobacillus* species population to a level equivalent to that present in the gastrointestinal tract of human milk-fed infants. This is important, since different *Lactobacillus* species exert different effects on the host. For example *L. delbrueckii* forms D-lactate which may result in acidosis in premature infants, whereas *L. paracasei* forms L-lactate.

Preferably the present *Lactobacillus* strain has at least 95, more preferably at least 97% identity of the 16S rRNA sequence when compared to the type strain of *L. paracasei* ATCC 25032 (Stackebrandt & Goebel, 1994, Int. J. Syst. Bacteriol. 44:846-849). The *Lactobacillus* used in the present invention preferably hybridises with the *L. paracasei* probe and gives a signal with the 5' nuclease assay method as described further on in this document.

Preferred *L. paracasei* strains are those isolated from the faeces of healthy human milk-fed infants. Several *L. paracasei* strains are commercially available from producers of lactic acid bacteria, but they can also be directly isolated from faeces, identified, characterised and produced. According to a preferred embodiment, the present composition contains at least *L. paracasei* selected from the group consisting of *L. paracasei* F19 (Arla, Sweden), *L. paracasei* LAFTI L26 (DSM Food Specialties, the Netherlands) and *L. paracasei* CRL 431 (Chr. Hansen, Denmark), LMG 12165 and LMG 11407.

The present composition preferably contains $10^2$ to $10^{13}$ colony forming units (cfu) of the *L. paracasei* per gram dry weight of the present composition, preferably $10^4$ to $10^{12}$, more preferably $10^5$ to $10^{10}$, most preferably from $10^5$ to $1 \times 10^9$ cfu *L. paracasei* per gram dry weight of the composition.

Preferably, the present composition contains $10^4$ to $10^{12}$, more preferably from $10^5$ to $10^{11}$, most preferably from $10^7$ to $5 \times 10^{10}$ colony forming units (cfu) *L. paracasei* per g of the total of saccharide A and B.

The dose of *L. paracasei* according to the present invention is preferably administered at a daily dose of $10^2$ to $10^{13}$, more preferably from $10^5$ to $10^{11}$, most preferably from $10^8$ to $5 \times 10^{10}$ colony forming units (cfu).

Combiotics

In still a further aspect, the present invention provides a composition comprising 5 to 16 en. % protein, 30 to 60 en. % fat, and 25 to 75 en. % carbohydrates comprising *Bifidobacterium breve* and *Lactobacillus paracasei*. The administration of the combination of these bacteria is believed to stimulate gastrointestinal health of the infant. The preferred compositional features, types of bacteria and medical indications as described in this document for the composition containing saccharide A and B and *B. breve* equally apply to the composition containing *B. breve* and *L. paracasei*. Saccharide A and/or saccharide B as described herein can be advantageously combined with the *B. breve* and *L. paracasei*. When *L. paracasei* is present in the composition of the invention, a single type of non-digestible saccharide may suffice for obtaining the desired effect. On the other hand, when *L. paracasei* is not present, the invention is particularly concerned with compositions containing saccharides A and B in a weight ratio between 95:5 and 99:1.

Other micro-organisms in addition to *B. breve* and/or *L. paracasei* may also be present, although no substantial further improvement will be obtained. Such other micro-organisms may comprise other *Bifidobacterium* species or other *Lactobacillus* species or even other lactic acid bacteria. Preferred Bifidobacteria are *B. longum* and/or *B. infantis*. Preferred Lactobacilli are *L. casei* and/or *L. acidophilus*.

Macronutrients

The present composition preferably contains fat, carbohydrate and protein.

Preferably the present composition contains a digestible carbohydrate selected from the group consisting of maltodextrin, starch, lactose, maltose, glucose, fructose, and sucrose. Preferably the present composition contains lactose. Preferably at least 35 wt. %, more preferably at least 50 wt. %, most preferably at least 75 wt. % of the digestible carbohydrate is lactose. When in liquid form, the present composition preferably comprises 6 to 19 g digestible carbohydrates per 100 ml, more preferably 6 to 10 g per 100 ml.

Preferably 10% to 80% of the total energy content of the present composition is provided by digestible carbohydrate. More preferably, the present composition contains 25 to 75 en. % carbohydrate. En. % is short for energy percentage and represents the relative amount each constituent contributes to the total caloric value of the preparation. The caloric value is provided by digestible carbohydrates, protein and fat.

Typical ingredients for use as a lipid source include animal fat, vegetable fat, and microbial fermentation oil. Fat is an important energy source and of utmost importance for a proper development of an infant. The present invention preferably contains linolenic acid (LA; an omega 6 fatty acid) and α-linolenic acid (ALA; an omega 3 fatty acid). The composition preferably comprises 0.3 to 1.5 g LA per 100 ml, and 0.05 to 5 g ALA per 100 ml. The weight ratio LA/ALA is preferably between 5 and 15. Preferably the present composition comprises long chain polyunsaturated fatty acids (LC PUFA), more preferably eicosapentaenoic acid (EPA) and/or docosahexaenoic acid (DHA). In a preferred embodiment the composition comprises arachidonic acid (ARA). Preferably the composition comprises 1 to 25 mg, more preferably 4 to 15 mg DHA per 100 ml. Preferably the composition comprises 2 to 50 mg, more preferably 6 to 30 mg ARA per 100 ml. The presence of LC-PUFA advantageously affects colonization of Lactobacilli and/or Bifidobacteria, especially of *Lactobacillus paracasei*. The present composition preferably comprises 30 to 60 en. % fat, more preferably 39 to 50 en. % fat. The composition preferably comprises 2.1 to 6.5 g fat per 100 ml.

Preferably the present composition comprises 5 to 16 en. %, more preferably 8 to 12 en. % protein. Preferably the present composition comprises a protein selected from the group consisting of casein, whey, skim milk, soy protein, pea protein, collagen, rice protein and/or corn protein. Preferably at least 25 wt. %, more preferably at least 50 wt. %, most preferably at least 90 wt. % of the total protein of the present composition is provided by hydrolysed protein and/or free amino acid. The use of protein hydrolysate and/or free amino acids reduces the risk of allergy, particularly cow's milk allergy. When the composition is in a liquid form, it preferably comprises 1.0 to 6.0 g, more preferably 1.0 to 2.5 g protein per 100 ml.

The present composition is preferably liquid. Stool irregularities (e.g. hard stools, insufficient stool volume, diarrhoea) are a major problem in many babies and ill subjects who receive liquid foods. Therefore, the present composition preferably has an osmolality between 50 and 500 mOsm/kg, more preferably between 100 and 400 mOsm/kg. With this osmolality, the present composition is particularly suitable for the treatment and/or prevention of diarrhoea.

It is also important that the present composition does not have an excessive caloric density, however still provides sufficient calories to feed the subject. Hence, the liquid food preferably has a caloric density between 10 and 250 kcal per 100 ml, even more preferably a caloric density of between 50 and 90 kcal/ml, most preferably between 60 and 71 kcal per 100 ml. Optimal caloric density also contributes to the reduced occurrence of diarrhoea.

The present compositions preferably comprises minerals, trace elements and vitamins, choline, taurine, carnitine, myo-inositol and/or mixtures thereof. Preferably the present composition contains taurine, which reduces the symptoms of asthma (*Adv. Exp. Med. Biol.* 2003 526:403-10). The taurine acts synergistically with the components in the present composition. Preferably the present composition comprises nucleotides. Preferably, the composition comprises cytidine 5'-monophospate, uridine 5'-monophospate, adenosine 5'-monophospate, guanosine 5'-monophospate, and inosine 5'-monophospate. Preferably the composition comprises 0.75 to 10, more preferably 1.5 to 5 mg nucleotides per 100 ml. The presence of nucleotides advantageously supports the survival and/or growth of Bifidobacteria and Lactobacilli, especially *B. breve* and/or *L. paracasei*. Preferably the present composition contains organic acids, flavours and/or colorants.

Applications

The composition according to the present invention has been found to be particularly useful as an infant nutrition. Also the composition is especially suitable for normalisation of the *Bifidobacterium* and/or the *Lactobacillus* population according to the species distribution in human milk-fed infants in the gastro-intestinal tract of infants which were non- or partly human milk-fed, in particular those which are prematurely born babies, maturely born babies, as well as infants which are in the adaptation period to solid food. Hence the present invention provides a method for providing nutrition to a human infant, said method comprising administering to the infant the present composition.

Preferably the infant has an age between 0 and 36 month, even more preferably between 0 and 18 month, most preferably between 0 and 12 months.

The gastrointestinal flora has an important effect on disorders such as gastrointestinal disorders, immune disorders and/or endocrine disorders. Hence, in a further aspect the present composition can be advantageously used in the manufacture of a medicament for use in a method for the prevention and/or treatment of gastro-intestinal disorders, immune disorders and/or endocrine disorders. Particularly allergy, allergic rhinitis, food hypersensitivity, atopic dermatitis, eczema, asthma, diarrhoea, intestinal inflammation, infection, constipation, intestinal cramps, colics, childhood obesity, and/or diabetes can be suitably treated with the present composition. In a preferred embodiment, the present invention provides a method for the treatment and/or prevention of atopic dermatitis, eczema, allergy and/or infection. In a preferred embodiment, the present invention provides a method for the treatment and/or prevention of allergy and/or infection. The present composition can be advantageously used in the manufacture of a medicament for use in a method for the prevention and/or treatment of gastro-intestinal disorders, immune disorders and/or endocrine disorders in an infant. The reduced occurrence of these diseases is due to the optimised intestinal flora, particularly the optimised *Bifidobacterium* species population and/or optimised *Lactobacillus* species population. The present invention particularly provides the use of the present composition for the manufacture of a composition for the prevention and/or treatment cow's milk allergy and/or infection.

EXAMPLES

Example 1: Clinical Study

In this study, the effect of an infant nutrition containing transgalactooligosaccharides, and fructopolysaccharides on intestinal Bifidobacteria and Lactobacilli was tested. The study was performed and the faecal samples were analysed as described in WO2005/039319

Infants were randomly allocated to one of two treatment groups: one group (SF-group) receiving a standard infant formula (Aptamil 1 Milupa) and; one group (GFSF-group) receiving standard formula supplemented with 0.72 g/100 ml transgalacto-oligosaccharides (GOS, VIVINAL® (Borculo Domo Ingredients, Netherlands) and 0.08 g/100 ml fructopolysaccharides (inulin, RAFTILINE®HP, Orafti, Belgium). A group of human milk-fed infants was included as a reference group (HMF group).

The relative quantification of the different *Bifidobacterium* and *Lactobacillus* species in faecal samples was determined by duplex 5' nuclease assays. The probes and primers were designed and validated for species belonging to *Bifidobacterium* as described in WO2005/039319 and for *Lactobacillus*. The probes and primers for *Lactobacillus* species are shown in table 1. F is the forward primer, R is the reverse primer and P is the probe. Table 2 shows the final optimal primer and probe concentrations used in the duplex 5' nuclease assays for *Lactobacillus*. The total amount of *Bifidobacterium* was also determined with help of FISH, like earlier described (Langendijk et al. 1995 Appl. Environ. Microbiol. 61:3069-75.).

TABLE 1

Designed primers and probes for use in the 5' nuclease assays.

| | Primers & Probes | Sequence (5'→3') |
|---|---|---|
| *L. acidophilus* | F | GAAAGAGCCCAAACCAAGTGATT (SEQ ID NO: 1) |
| | R | CTTCCCAGATAATTCAACTATCGCTTA (SEQ ID NO: 2) |
| | P | TACCACTTTGCA GTCCTACA (SEQ ID NO: 3) |
| *L. casei* | F | CTATAAGTAAGCTTTGATCCGGAGATTT (SEQ ID NO: 4) |
| | R | CTTCCTGCGGGTACTGAGATGT (SEQ ID NO: 5) |
| | P | ACAAGCTATGAATTCACTTGC (SEQ ID NO: 6) |
| *L. delbrueckii* | F | CACTTGTACGTTGAAAACTGAATATCTTAA (SEQ ID NO: 7) |
| | R | CGAACTCTCTCGGTCGCTTT (SEQ ID NO: 8) |
| | P | CCGAGAATCATTGAGATC (SEQ ID NO: 9) |
| *L. fermentum* | F | AACCGAGAACACCGCGTTAT (SEQ ID NO: 10) |
| | R | ACTTAACCTTACTGATCGTAGATCAGTCA (SEQ ID NO: 11) |
| | P | TAATCGCATACTCAACTAA (SEQ ID NO: 12) |
| *L. paracasei* | F | ACATCAGTGTATTGCTTGTCAGTGAATAC (SEQ ID NO: 13) |
| | R | CCTGCGGGTACTGAGATGTTTC (SEQ ID NO: 14) |
| | P | TGCCGCCGGCCAG (SEQ ID NO: 15) |
| *L. plantarum* | F | TGGATCACCTCCTTTCTAAGGAAT (SEQ ID NO: 16) |
| | R | TGTTCTCGGTTTCATTATGAAAAAATA (SEQ ID NO: 17) |
| | P | ACATTCTTCGAAACTTTGT (SEQ ID NO: 18) |
| *L. reuteri* | F | ACGAGAACACCGCGTTATTT (SEQ ID NO: 19) |
| | R | CATAACTTAACCTAAACAATCAAAGATTGTCT (SEQ ID NO: 20) |
| | P | ATCGCTAACTCAATTAAT (SEQ ID NO: 21) |
| *L. rhamnosus* | F | CGGCTGGATCACCTCCTTT (SEQ ID NO: 22) |
| | R | GCTTGAGGGTAATCCCCTCAA (SEQ ID NO: 23) |
| | P | CCTGCACACACGAAA (SEQ ID NO: 24) |
| Genus *Lactobacillus* | F | TGGATGCCTTGGCACTAGGA (SEQ ID NO: 25) |
| | R | AAATCTCCGGATCAAAGCTTACTTAT (SEQ ID NO: 26) |
| | P | TATTAGTTCCGTCCTTCATC (SEQ ID NO: 27) |
| All bacteria* | F | TCCTACGGGAGGCAGCAGT (SEQ ID NO: 28) |
| | R | GGACTACCAGGGTATCTAATCCTGTT (SEQ ID NO: 29) |
| | P | CGTATTACCGCGGCTGCTGGCAC (SEQ ID NO: 30) |

*Probes and primers were derived from Nadkarni et al, 2002, Microbiology 148:257-266.

TABLE 2

Optimised final primer and probe concentrations used in the different duplex 5' nuclease assays

| Target | 5' nuclease assay | Forward Primer (nM) | Reverse Primer (nM) | Probe (nM) |
|---|---|---|---|---|
| L. acidophilus | L. acidophilus | 900 | 900 | 200 |
|  | Genus Lactobacillus | 900 | 900 | 200 |
| L. casei | L. casei | 900 | 900 | 200 |
|  | Genus Lactobacillus | 300 | 300 | 50 |
| L. delbrueckii | L. delbrueckii | 300 | 300 | 100 |
|  | Genus Lactobacillus | 900 | 900 | 200 |
| L. fermentum | L. fermentum | 300 | 300 | 100 |
|  | Genus Lactobacillus | 300 | 300 | 100 |
| L. paracasei | L. paracasei | 300 | 300 | 100 |
|  | Genus Lactobacillus | 300 | 300 | 100 |
| L. plantarum | L. plantarum | 300 | 300 | 100 |
|  | Genus Lactobacillus | 300 | 300 | 100 |
| L. reuteri | L. reuteri | 300 | 300 | 100 |
|  | Genus Lactobacillus | 900 | 900 | 200 |
| L. rhamnosus | L. rhamnosus | 900 | 450 | 200 |
|  | Genus Lactobacillus | 150 | 100 | 100 |
| Genus Lactobacillus | Genus Lactobacillus | 600 | 600 | 100 |
|  | All bacteria | 300 | 300 | 100 |

Results:

The percentage of the genus *Bifidobacterium* as a percentage of total bacteria was 75, 47, and 68% in the HMF, SF, and GFSF group, after a 6 week feeding period, respectively. The amount of Lactobacilli was than 3.9, 0.4, and 4.2%, respectively. The differences between the GFSF and SF group were statistically significant.

In table 3 the percentage of *Bifidobacterium* species relative to the total amount of to Bifidobacteria is shown.

TABLE 3

Percentage of *Bifidobacterium* species with respect to the total number of *Bifidobacteria* in the faeces of human milk-fed infants (HMF) and infants who received a standard formula (SF) or a standard formula supplemented with TOS/polyfructose (GFSF) after a 6 week feeding period.

| Species | HMF % (SE) | GFSF % (SE) | SF % (SE) |
|---|---|---|---|
| B. catenulatum | 1.9 (0.6) | 1.4 (1.0)[b] | 8.1 (4.1)[b] |
| B. adolescentis | 0.3 (0.9)[a] | 0.2 (0.1)[a] | 2. (1.9) |
| B. breve | 11.7 (9.6) | 5.4 (10.8) | 4.9 (10.7)[a] |
| B. longum | 7.3 (13.9) | 5.4 (10.7) | 6.2 (9.4) |
| B. bifidum | <0.1 (0.0) | <0.1 (0.0) | <0.1 (0.0) |
| B. angulatum | <0.0 (0.0) | <0.1 (0.2) | <0.1 (0.0) |
| B. infantis | 32.0 (18.9) | 32.1 (20.0) | 37.8 (18.4) |
| B. dentium | <0.1 (0.0) | <0.1 (0.0) | <0.1 (0.0) |

[a] a significant decrease during the study period
[b] a significant difference between the GFSF and SF group.

A large variety of *Bifidobacterium* species is present in the three different groups. Furthermore, a significant decrease in *B. adolescentis* is visible in human milk-fed infants and in infants receiving GFSF contrary to infants receiving a standard formula. After 6 weeks of feeding *B. adolescentis* is much higher in SF-fed babies than in babies which were GFSF or human milk-fed. Analyses of the faecal samples of GFSF infants shows a large variety in the Bifidobacteria flora similar to human milk-fed infants. The profiles of human milk-fed infants and infants receiving GFSF also showed less *B. catenulatum* (+*B. pseudocatenulatum*) than the profile of infants receiving a standard formula. *B. infantis*, and *B. longum* seems to be predominant in human milk-fed infants as well as in infants receiving a standard formula (SF) or a standard formula supplemented with prebiotics (GFSF). Also *B. breve* was dominant in all three groups, but in the group receiving human milk *B. breve* as a % of total Bifidobacteria was higher (11.7%) as in the SF (4.9%) and GFSF (5.4%) group.

In table 4 the species distribution of Lactobacilli in the faeces of the differently fed infants is given.

TABLE 4

Percentage of *Lactobacillus* species with respect to the total number of *Lactobacilli* in the faeces of human milk-fed infants (HMF) and infants who received a standard formula (SF) or a standard formula supplemented with TOS/fructopoly-saccharides (GFSF) after a 6 week feeding period.

| Species | HMF % (SE) | GFSF % (SE) | SF % (SE) |
|---|---|---|---|
| L. acidophilus | 23.5 (4.5)[a] | 24.5 (3.9)[a] | 19.2 (4.1) |
| L. casei | 6.0 (1.8)[a] | 10.7 (2.5)[a] | 8.3 (2.0)[a] |
| L. delbrueckii | <0.001 (0.00) | 0.01 (0.01)[bc] | 6.9 (2.8)[ac] |
| L. fermentum | <0.001 (0.00) | <0.001 (0.00) | 0.05 (0.03) |
| L. paracasei | 22.1 (6.1)[a] | 16.8 (4.2)[a] | 5.6 (3.3) |
| L. plantarum | <0.001 (0.00) | <0.001 (0.00) | <0.001 (0.00) |
| L. reuteri | 1.4 (0.6) | 1.3 (0.4) | 6.4 (3.2) |
| L. rhamnosus | <0.001 (0.00) | <0.001 (0.00) | <0.001 (0.00) |

[a] a significant increase during the study period
[b] a significant decrease during the study period
[c] a significant difference between the GFSF and SF group.

As can be seen in table 4 a large variety of *Lactobacillus* species is present in the human milk-fed and standard formula-fed infants. However, the species distribution is not similar in human milk-fed and in standard formula fed infants. A decrease in *L. delbrueckii* is visible in human milk-fed infants contrary to infants receiving a standard formula, where an increase is observed. After 6 weeks of feeding a significant increase of *L. acidophilus, L. casei,* and *L. paracasei* is observed in human milk-fed infants, whereas the increase of *L. acidophilus* and *L. paracasei* is not significant in formula-fed infants. Compared to human-milk-fed infants standard formula-fed infants tend to have relative higher concentrations of *L. fermentum* and *L. reuteri*. Surprisingly, analyses of the faecal samples of GFSF infants shows a large variety in the *Lactobacillus* flora similar to human milk-fed infants. The species distribution in GFSF fed infants is very similar to that observed in human milk-fed infants. As is observed in human milk-fed infants, GFSF fed infants have relatively decreased amounts of *L. delbrueckii, L. reuteri* and *L. fermentum* and increased amounts of *L. acidophilus, L. casei* and *L. paracasei*. The relative amounts of *L. paracasei* in GFSF fed infants tends to be lower than those of human milk-fed infants, however.

These results are indicative that feeding a mixture of non-digestible saccharides A and B, which comprise at least 60, especially at least 98 mol % of one or more monosaccharide units selected from the group consisting of galactose, fructose and glucose, and which A and B differ in chemical structure results in a species distribution of Bifidobacteria and Lactobacilli similar to those observed in human milk-fed infants (i.e. relatively decreased *B. adolescentis, B. catenulatum, L. delbrueckii, L. fermentum,* and/or *L. reuteri* and relatively increased *B. longum, B. infantis, B. breve L. casei, L. paracasei* and/or *L. acidophilus*). Also these results are indicative that administering this mixture of non-digestible saccharide A and B in combination with *B. breve* or with *B. breve* plus *L. paracasei* will restore the intestinal flora in infants in such a way that it mimics that of human milk-fed infants regarding the *Bifidobacterium* and *Lactobacillus* species distribution, making the intestinal flora more reminiscent to those of human milk-fed infants will have a beneficial effect on treatment and/or prevention of gastrointestinal disorders, immune disorders and/or endocrine disorders in infants.

Example 2: Effect on Allergic Reaction

Specific pathogen free male BALB/c mice were obtained from Charles River (Maastricht, the Netherlands). Food and water was provided ad libitum and the mice were used when 6-9 weeks of age.

Mice were sensitised by two i.p. injections with 10 μg ovalbumin adsorbed onto 2.25 mg aluminium hydroxide in 100 μl saline or saline alone on days 0 and 7. Mice were challenged on days 35, 38, and 41 by inhalation of ovalbumin aerosols in a plexiglass exposure chamber for 20 minutes. The aerosols were generated by nebulising an ovalbumin solution (10 mg/ml) in saline using a Pari LC Star nebulizer (Pari respiratory Equipment, Richmond, Va., USA).

Mice were treated daily with $1 \times 10^9$ cfu *Bifidobacterium breve* and 25 mg of a mixture of transgalacto-oligosaccharides and fructopolysaccharides (9:1) (TOS/fructopolysaccharide mixture of example 2) orally via gavage (0.2 ml, physiological salt solution) starting at day 28 up to the end of the experiment (i.e. day 42). As a control 0.2 ml physiological salt solution was administered via gavage.

Airway responsiveness to inhaled nebulised methacholine was determined 24 hours after the final aerosol challenge, in conscious, unrestrained mice using whole body plethysmography (BUXCO, EMKA, Paris, France). The airway response was expressed as enhanced pause (PenH).

Results: Measurements on airway hyper-responsiveness show that compared to control the mice receiving the *B. breve*, TOS and fructopolysaccharide show a statistically reduced airway hyper-responsiveness, indicative of a lowered asthmatic reaction. In FIG. 1 the airway hyper-responsiveness is plotted as relative PenH (enhanced pause) versus the methacholine concentration for mice receiving a combination of *B. breve*+a mixture of TOS/fructopolysaccharide and a control group of mice receiving saline instead. The plotted values of relative PenH are obtained after subtraction of the blank values obtained for mice not ovalbumin-sensitised and normalisation to the value obtained for the control group at the highest concentration of methacholine.

Example 3

An infant milk formula containing per 100 ml final product a viscosity of 2.0±0.2 mPa·s and:

| | |
|---|---|
| 13 energy % protein (casein and whey) | 2.2 g |
| 49 energy % digestible carbohydrates | 8.6 g |
| 37 energy % fat | 3.0 g |
| TOS (present in VIVINAL ®GOS) (average DP between 2 and 4) | 0.72 g |
| FOS (Raftiline HP) (average DP between 23-25) | 0.08 g |
| *B. breve* | $1.6 \times 10^8$ cfu |
| *L. paracasei* | $1.6 \times 10^8$ cfu |

The invention claimed is:

1. An infant formula composition having a viscosity between 1 and 6 mPa·s and a caloric density between 10 and 250 kcal per 100 ml, comprising:
   a. *Bifidobacterium breve*;
   b. a first non-digestible saccharide having a degree of polymerisation between 2 and 8 and at least 60 mol % of the total monosaccharide units of the first non-digestible saccharide are galactose; and
   c. a second non-digestible saccharide having a degree of polymerisation between 8 and 100 and at least 60 mol % of the total monosaccharide units of the second non-digestible saccharide are fructose; wherein
      i. the average degree of polymerisation of the first non-digestible saccharide is at least 5 monosaccharide units lower than the average degree of polymerisation of the second non-digestible saccharide;
      ii. the concentration of the first saccharide is between 50 mg and 2 g per 100 ml and the concentration of the second saccharide is between 5 mg and 1 g per 100 ml; and
      iii. a non-digestible saccharide is a saccharide that is not digested in the upper intestinal tract of a human infant.

2. The infant formula composition according to claim 1 wherein the viscosity is 2±0.2 mPa·s.

3. The infant formula composition according to claim 1, wherein the weight ratio between the first non-digestible saccharide and the second non-digestible saccharide is between 4 and 24.

4. The infant formula composition according to claim 1 further comprising *Lactobacillus paracasei*.

5. The infant formula composition according to claim 1, wherein the first non-digestible saccharide comprises at least 67 mol % galactose units based on the total monosaccharide units of the first non-digestible saccharide.

6. The infant formula composition according to claim 1, wherein the first non-digestible saccharide comprises at least 75 mol % galactose units based on the total monosaccharide units of the first non-digestible saccharide.

7. The infant formula composition according to claim 1, wherein the second non-digestible saccharide comprises at least 67 mol % fructose units based on the total monosaccharide units of the second non-digestible saccharide.

8. The infant formula composition according to claim 1, wherein the second non-digestible saccharide comprises at least 75 mol % fructose units based on the total monosaccharide units of the second non-digestible saccharide.

9. The infant formula composition according to claim 1, wherein the first non-digestible saccharide comprises at least 75 mol % galactose units based on the total monosaccharide units of the first non-digestible saccharide the second non-digestible saccharide comprises at least 75 mol % fructose units based on the total monosaccharide units of the second non-digestible saccharide.

10. The infant formula composition according to claim 1, comprising $10^2$ to $10^{13}$ colony forming units of *Bifidobacterium breve* per gram of dry weight of the composition.

11. The infant formula composition according to claim 1, wherein:
    (i) 5 to 16 percent of the total energy of the composition is derived from protein,
    (ii) 30 to 60 percent of the total energy of the composition is derived from fat, and
    (iii) 25 to 75 percent of the total energy of the composition is derived from carbohydrates.

12. The infant formula composition according to claim 1, comprising between 0.1 and 2 g of the first non-digestible saccharide per 100 ml and between 10 mg and 1 g of the second non-digestible saccharide per 100 ml.

13. The infant formula composition according to claim 12, comprising between 0.1 and 2 g per 100 ml of the first non-digestible saccharide and between 10 mg and 1 g per 100 ml of the second non-digestible saccharide.

14. The infant formula composition according to claim 13, comprising between 0.5 and 2 g per 100 ml of the first non-digestible saccharide and between 50 mg and 1 g per 100 ml of the second non-digestible saccharide.

15. The infant formula composition according to claim 1, comprising at least 0.75 mg nucleotides per 100 ml.

16. The infant formula composition according to claim 4, wherein:
   (i) 5 to 16 percent of the total energy of the composition is derived from protein,
   (ii) 30 to 60 percent of the total energy of the composition is derived from fat, and
   (iii) 25 to 75 percent of the total energy of the composition is derived from carbohydrates.

17. A method for providing nutrition to an infant, comprising administering to the infant a nutritional composition having a viscosity between 1 and 6 mPa·s and a caloric density between 10 and 250 kcal per 100 ml and comprising:
   a. *Bifidobacterium breve;*
   b. a first non-digestible saccharide having a degree of polymerisation between 2 and 8 and at least 60 mol % of the total monosaccharide units of the first non-digestible saccharide are galactose; and
   c. a second non-digestible saccharide having a degree of polymerisation between 8 and 100 and at least 60 mol % of the total monosaccharide units of the second non-digestible saccharide are fructose;
   wherein the average degree of polymerisation of the first non-digestible saccharide is at least 5 monosaccharide units lower than the average degree of polymerisation of the second non-digestible saccharide and the concentration of the first saccharide is at least 50 mg per 100 ml and the concentration of the second saccharide is at least 5 mg per 100 ml, and wherein a non-digestible saccharide is a saccharide that is not digested in the upper intestinal tract of a human infant.

* * * * *